US008835843B2

(12) United States Patent
Lechner

(10) Patent No.: US 8,835,843 B2
(45) Date of Patent: Sep. 16, 2014

(54) PARTICLE BEAM SYSTEM AND METHOD OF PROCESSING A TEM-SAMPLE

(71) Applicant: Carl Zeiss Microscopy GmbH, Jena (DE)

(72) Inventor: Lorenz Lechner, Koenigsbronn (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 14/057,002

(22) Filed: Oct. 18, 2013

(65) Prior Publication Data

US 2014/0110577 A1   Apr. 24, 2014

(51) Int. Cl.
| | |
|---|---|
| H01J 37/00 | (2006.01) |
| H01J 37/28 | (2006.01) |
| H01J 37/26 | (2006.01) |
| H01J 37/305 | (2006.01) |
| G01N 1/32 | (2006.01) |

(52) U.S. Cl.
CPC ............... *H01J 37/26* (2013.01); *H01J 37/28* (2013.01); *G01N 1/32* (2013.01); *H01J 2237/31745* (2013.01); *H01J 37/3056* (2013.01)
USPC ........... 250/307; 250/306; 250/310; 250/311; 250/492.3

(58) Field of Classification Search
CPC ............. H01J 2237/31745; H01J 2237/31749; H01J 37/20; H01J 2237/20207; H01J 2237/20214; G01N 1/32; G01N 1/28
USPC ............ 250/306, 307, 310, 311, 492.1–492.3
See application file for complete search history.

(56) References Cited

U.S. PATENT DOCUMENTS

| | | | |
|---|---|---|---|
| 5,770,861 A * | 6/1998 | Hirose et al. ................... | 250/310 |
| 6,855,938 B2 | 2/2005 | Preikszas et al. | |
| 8,487,270 B2 * | 7/2013 | Zeile et al. ............... | 250/442.11 |
| 2002/0050565 A1 | 5/2002 | Tokuda et al. | |
| 2008/0296498 A1 * | 12/2008 | Hong ............................ | 250/311 |

(Continued)

FOREIGN PATENT DOCUMENTS

| | | |
|---|---|---|
| EP | 2043131 | 4/2009 |
| EP | 2413126 | 2/2012 |

OTHER PUBLICATIONS

Lechner, et al ("Improved Focused Ion Beam Target Preparation of (S)TEM Specimen—A Method for Obtaining Ultrathin Lamellae" Microscopy and Microanalysis, vol. 18, issue 02, Apr. 2012, pp. 379-384, published online Mar. 21, 2012.*

(Continued)

*Primary Examiner* — Michael Maskell
(74) *Attorney, Agent, or Firm* — Morris & Kamlay LLP

(57) ABSTRACT

A method of processing a TEM-sample, wherein the method comprises: mounting an object in a particle beam system such that the object is disposed, in an object region of the particle beam system; directing of a first particle beam onto the object region from a first direction, wherein the first particle beam is an ion beam; and then rotating the object about an axis by 180°, wherein the following relation is fulfilled:

$$35° \leq \alpha \leq 55°,$$

wherein $\alpha$ denotes a first angle between the first direction and the axis; and then directing of the first particle beam onto the object region from the first direction; wherein material is removed from the object during the directing of the first particle beam onto the object region. Furthermore, a second particle beam may be directed onto the object region, and particles emanating from the object region can be detected.

18 Claims, 7 Drawing Sheets

(56) References Cited

U.S. PATENT DOCUMENTS

| | | | | |
|---|---|---|---|---|
| 2008/0315088 | A1* | 12/2008 | Takahashi et al. | 250/306 |
| 2011/0140006 | A1* | 6/2011 | Tomimatsu et al. | 250/492.21 |
| 2011/0226947 | A1* | 9/2011 | Takahashi et al. | 250/307 |
| 2012/0189813 | A1* | 7/2012 | Lechner et al. | 428/156 |
| 2012/0305765 | A1* | 12/2012 | Zeile et al. | 250/307 |
| 2013/0248354 | A1* | 9/2013 | Keady et al. | 204/192.33 |

OTHER PUBLICATIONS

Office Action in German patent application No. 10 2012 020 478.7 dated Jul. 9, 2013, with English language translation.

Lechner et al.,"Improved Focused Ion Beam Target Preparation of (S)TEM Specimen—A Method for Obtaining Ultrathin Lamellae", Microscopy and Microanalysis, 2012, pp. 379-384.

* cited by examiner

PARTICLE BEAM SYSTEM AND METHOD OF PROCESSING A TEM-SAMPLE

CROSS-REFERENCE TO RELATED APPLICATIONS

This application claims priority of Patent Application No. 10 2012 020 478.7, filed Oct. 18, 2012 in Germany, the entire contents of which are incorporated by reference herein.

FIELD

The present invention relates to a particle beam system and a method of processing a TEM-sample.

BACKGROUND

A transmission electron microscope (TEM) allows for material analyses of very high spatial resolution. For example, structures with feature sizes of 1 nm or less can be resolved. For this purpose, a so-called TEM-sample must be formed of the material to be analyzed, wherein the TEM-sample is at least in part thin so that electrons of the electron beam generated by the transmission electron microscope can traverse the material. Such thin objects are also referred to as TEM-lamellae and exhibit a thickness of, for example, 100 nm or less. The manufacture of such TEM-samples is elaborate and difficult.

A specific kind of TEM-sample is known from US 2012/0185813 A1, wherein the full disclosure of this document is incorporated herein by reference. An example of a TEM-sample known from this reference is schematically illustrated in FIG. 1. For manufacturing the TEM-sample 101 illustrated in FIG. 1, a cuboid-shaped material-block 103 is cut out of a substrate, wherein the material-block contains the region to be analyzed using the transmission electron microscope. The cuboid-shaped material-block can exhibit thicknesses of 0.1 µm to 500 µm and lengths and widths of 5 µm to 1000 µm, for example. Here, the thickness of the cuboid-shaped material-block 103 is too large in order to be traversed appropriately by electrons in a transmission electron microscope. Hence, a strip-shaped recess is formed in each of two opposing flat sides of the cuboid, wherein the recesses extend at an angle δ of, for example, 45° with respect to an edge of the cuboid such that an angle ε between the directions of extension of the strip-shaped recesses 105 amounts to a value of, for example, 90°. A depth of the recesses 105 is somewhat smaller than half the thickness of the cuboid 103 so that a hatched region 107 in FIG. 1, the region of which the recesses 105 cross and overlap, provides a slight material thickness which is equal to the thickness of the cuboid 103 minus the thicknesses of both the recesses 105. By appropriate forcing of the recesses 105, for example, by removing material using a focused ion beam, it is possible to configure the material thickness in the region 107 small such that the material in the region 107 can be analyzed using a transmission electron microscope.

The TEM-sample illustrated in FIG. 1 has the advantage that, due to the surrounding regions of the cuboid 103, the region 107 of thin material is bared by means of a frame and protected against the deformation, wherein the frame can be attached to manipulators and object mounts without damaging the comparatively fragile thin region 107.

US 2012/0185813 A1 discloses apparatuses and methods for manufacturing a TEM-sample illustrated in FIG. 1. Nevertheless, it is desirable to have further apparatuses and methods available which allow manufacturing of such TEM-samples.

SUMMARY

Embodiments of the present invention provide a particle beam system and a method of processing a TEM-sample providing a comparatively simple and reliable manufacture of a TEM-sample and its analysis using a transmission electron microscope.

According to certain embodiments, a particle beam system comprises a first particle beam column configured to generate a first particle beam incident onto an object region from a first direction, wherein the first particle beam is an ion beam, a second particle beam column configured to generate a second particle beam incident onto an object region from a second direction and an object mount configured to mount an object in the object region, wherein the object mount comprises a shaft rotatable with respect to the first particle beam column about an axis of rotation, wherein the following relation is fulfilled: $35° \leq \alpha \leq 55°$, wherein $\alpha$ denotes a first angle between the first direction and the axis of rotation.

The first particle beam, which is an ion beam, generated by the first particle beam column serves to remove material from a TEM-sample to be manufactured or to be analysed. On the one hand, this removing of material may be used, to form the strip-shaped recesses previously described in the context of FIG. 1. Here, the ion beam may be, for example, a focused gallium-ion beam. Furthermore, a process-gas may be fed to a location on the object processed by the ion beam, wherein the process-gas is excited by ions of the ion beam or secondary particles dissolved from the object by the ion beam, forms a compound with material of the object and, thereby, dissolves material from the object (assisted ion beam etching).

On the other hand, the ion beam may be used to remove impurities on the TEM-sample generated by, for example, oxidation. Here, the ion beam may be, for example, an argon-ion beam.

The second particle beam generated by the second particle beam column may be used to monitor and to control the method of processing the object using the first particle beam. Here, the particle beam system may comprise a detector in order to detect secondary particles emerging from the object. Furthermore, the second particle beam column may comprise one or multiple beam deflectors in order to modify an impinging location of the second particle beam onto the object so that secondary particles emerging from the object may be detected spatially resolved. In particular, the second particle beam may be scanned across the object region systematically, wherein a microscopic image of the scanned object region is created from intensities of detected secondary particles emerging from the object. The particles of the second particle beam having interacted with the object may be electrons backscattered from the object itself and electrons transmitted through the object.

The second particle beam may be an ion beam as well, for example, a helium-ion beam. Furthermore, the second particle beam may be an electron beam, and the second particle beam column may be configured to be an electron microscope. Here, the second particle beam column may comprise a scanning electron microscope (SEM). Such a SEM, together with the first particle beam column, is preferably used in order to form the strip-shaped recesses in the TEM-sample illustrated with reference to FIG. 1. Here, the first and the second particle beam columns are integrated in a particle beam system, also referred to by cross-beam-system or dual-beam-system. Here, $\gamma$ denotes a third angle between the first direction from which the first particle beam is incident onto the object region and the second direction from which the second particle beam is incident onto the object region, wherein γ amounts to a value between 20° and 90°, in particular between 30° and 60° and in particular between 40° and 55°. This particle beam system may comprise a scanning electron microscope comprising a detector detecting electrons generated by the scanning electron microscope having transmitted the object. Using such a scanning transmission electron microscope (STEM) transmission-electron-microscopic analyses may be performed directly without having to transfer the object into a separate transmission electron microscope.

The second particle beam column may also comprise a transmission electron microscope (TEM) configured to perform the transmission-electron-microscopic analysis of the TEM-sample. Here, the first particle beam preferably serves to remove impurities from the TEM-samples. Furthermore, γ denotes a third angle between the first direction from which the first particle beam is directed onto the object region and the second direction from which the second particle beam is directed onto the object region is preferably larger than 80°, in particular larger than 85° and according to a special embodiment equal to 90°.

The angle α between the first direction from which the first particle beam is incident onto the object region and the axis of rotation of the object mount is chosen such that the TEM-sample mounted to the object mount may be transferred from a first position into a second position by rotating the object mount by 180° about the axis of rotation, wherein, in the first position, one of the strip-shaped recesses illustrated with reference to FIG. 1 may be processed by the first particle beam, and, in the second position, the other one of both the strip-shaped recesses may be processed by the first particle beam. Thus, in a particularly easy way, it is possible to perform at least one of forming both the strip-shaped recesses using the first particle beam and removing impurities from the TEM-sample comprising previously formed strip-shaped recesses.

Accordingly, an embodiment of a method of processing a TEM-sample may comprise the following elements: mounting an object to an object mount, disposing the object in a first particle beam system so that the object is disposed in an object region of the first particle beam system, a first directing of a first particle beam onto the object region from a first direction, wherein the first particle beam is an ion beam, and then rotating the object about an axis by 180°, wherein the following relation is fulfilled:

$$35° \leq \alpha \leq 55°,$$

wherein α denotes a first angle between the first direction and the axis, and then a second directing of the first particle beam onto the object region from the first direction, wherein material is removed from the object during the first directing and the second directing of the first particle beam onto the object region.

Here, the first directing and the second directing of the first particle beam onto the object region may be used to form strip-shaped recesses in the object or to clean impurities, for example, oxides from the object.

Here, the rotating of the object about the axis may be performed by a single step of rotation about an axis of rotation. However, it is also possible to perform this rotating by multiple steps of movement which may comprise, for example, multiple consecutively executed steps of rotation about distinct axes of rotation and steps of translation in one or multiple directions.

Furthermore, the method may comprise a third directing of a second particle beam onto the object region and a detecting of particles emanating from the object region. Here, at least one of the first directing and the second directing of the first particle beam onto the object region may be performed based on the secondary particles detected during the third directing of the second particle beam onto the object region. As previously described, the second particle beam may be an ion beam or an electron beam, and microscopic images may be created from spatially resolved intensities detected from secondary particles emanating from the object region in order to monitor the process of forming the strip-shaped recesses or in order to perform the transmission-electron-microscopic analysis of the TEM-sample.

Furthermore, it is possible to manufacture the TEM-sample in the first particle beam system initially and then to transfer the TEM-sample into a second particle beam system in order to conduct further processing therein which also comprises a rotating of the object about an axis by 180° in the second particle beam system. The second particle beam system may comprise, for example, a TEM serving for a transmission-electron-microscopic analysis of the TEM-sample formed in the first particle beam system, wherein an ion beam is used therein in order to remove impurities from the TEM-sample which arose during the transfer of the TEM-sample from the first particle beam system into the second particle beam system.

Here, the method may further comprise the following elements: disposing the object in a second particle beam system so that the object is disposed in an object region of the second particle beam system; a fourth directing Of a third particle beam onto the object region from a fourth direction, wherein the third particle beam is an ion beam; and then rotating the object about an axis by 180°, wherein the following relation is fulfilled:

$$35° \leq \alpha \leq 55°,$$

wherein α denotes the first angle between the fourth direction and the axis; and then a fifth directing of the third particle bears onto the object region from the fourth direction; and then a sixth directing of a fourth particle beam onto the object region and detecting the particles transmitted through the object; wherein material is removed from the object during the fourth directing and the fifth directing of the third particle beam onto the object region and wherein the fourth particle beam is an electron beam generated by a TEM.

Here, the ion beam, may be an argon-ion beam in particular.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
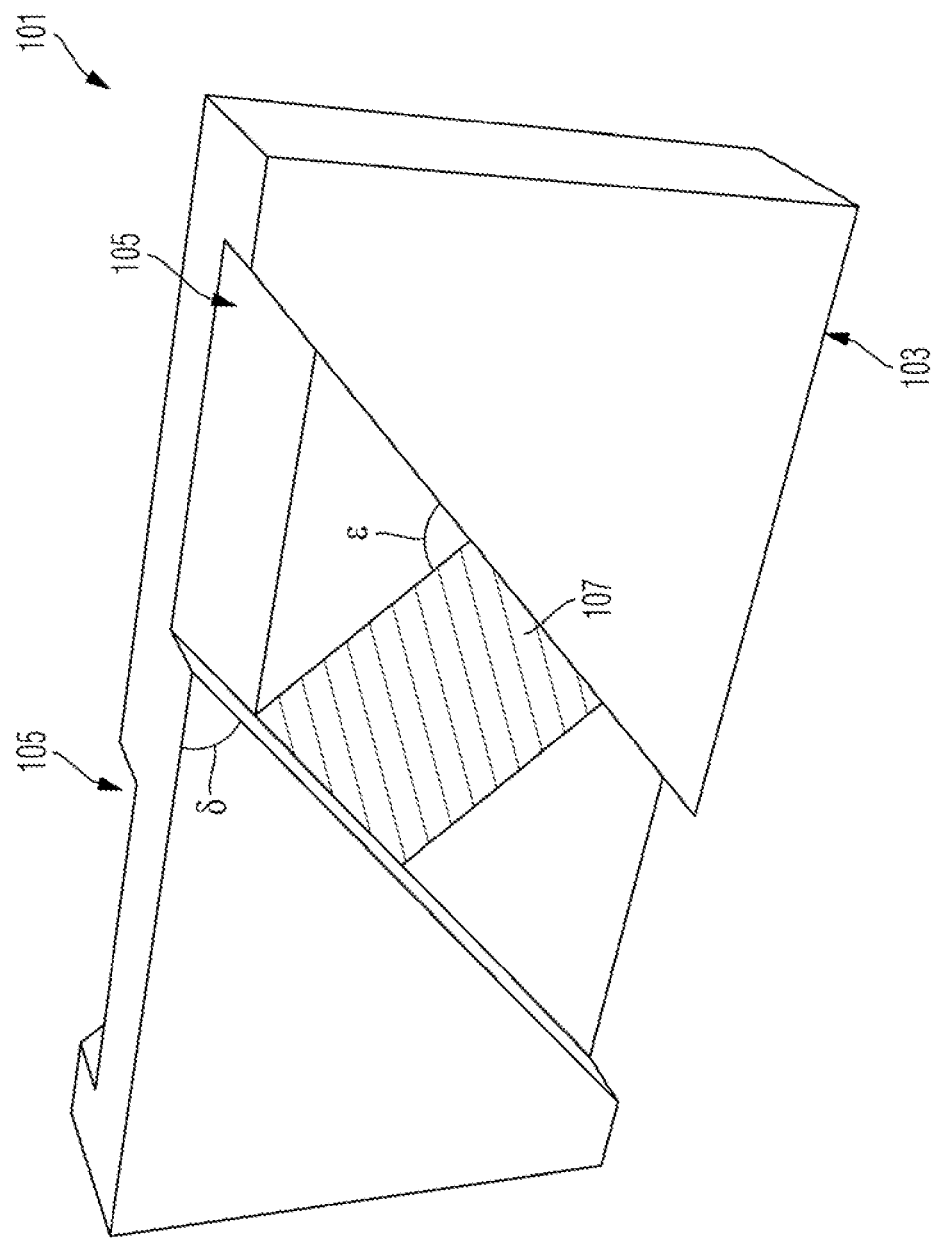
FIG. 1 is a schematic, perspective illustration of a TEM-sample.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

Figure 2:
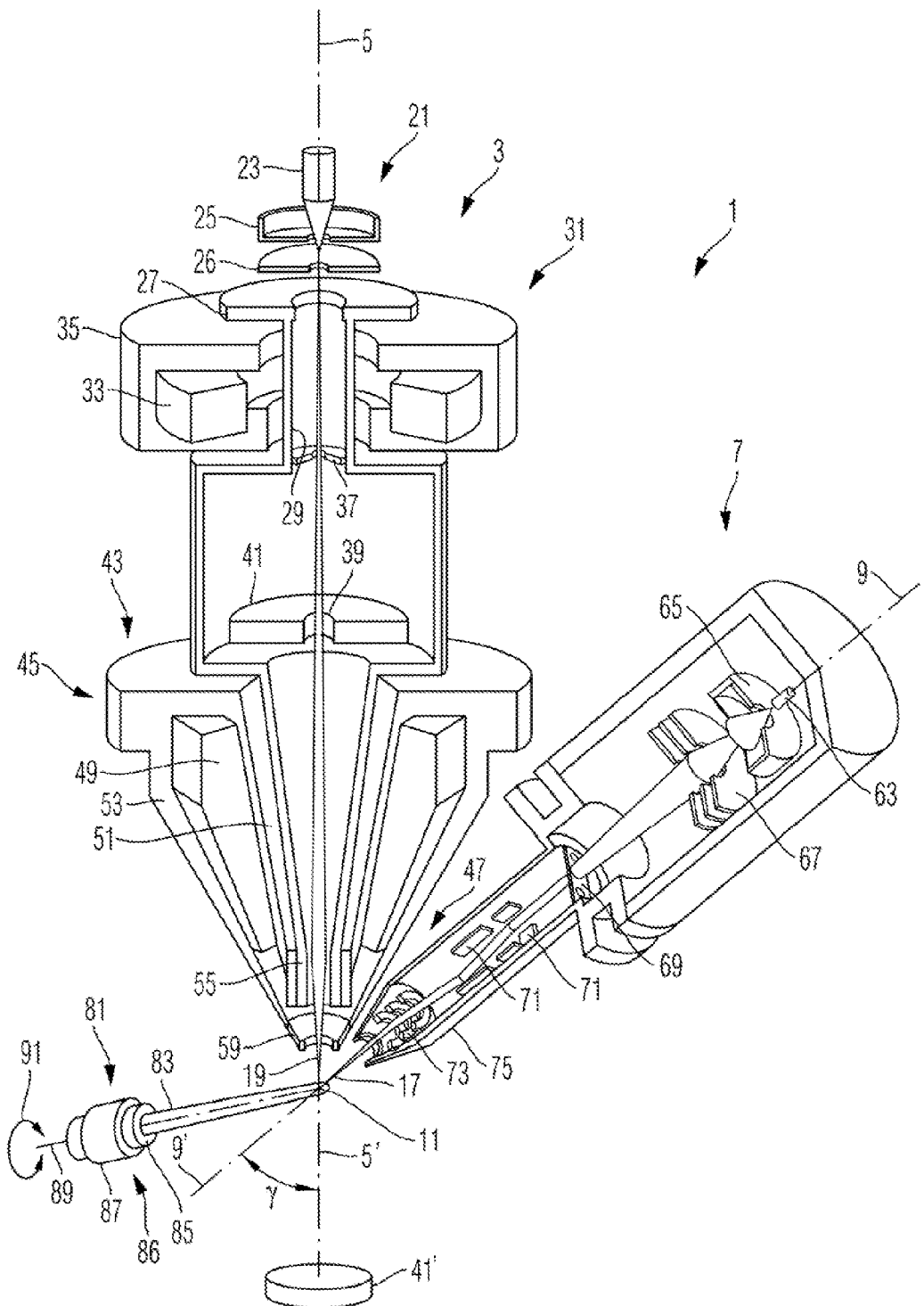
FIG. 2 is a schematic illustration of a particle beam system configured to manufacture the TEM-sample illustrated in FIG. 1.

In a perspective and schematically simplified illustration, FIG. 2 illustrates a particle beam system, with which a TEM-sample as illustrated in FIG. 1 can be manufactured. The particle beam system 1 comprises an electron microscopy system 3 with a main axis 5 and an ion beam processing system 7 with a main axis 9. The main axis 5 of the electron microscopy system 3 and the main axis 9 of the ion beam processing system 7 intersect in an object region 11 at an angle γ amounting to a value between, for example, 45° and 55° so that an object to be manufactured can both be processed by an ion beam 17 emitted along the main axis 9 of the ion beam processing system 7 and be analyzed using an electron beam 19 emitted along the main axis 5 of the electron microscopy system 3.

Here, the electron microscopy system 3 configured to generate the primary-electron beam 19 comprises an electron source 21 schematically illustrated by a cathode 23, a thereof distantly disposed suppressor electrode 25 and a thereof distantly disposed contact electrode 26. Furthermore, the electron microscopy system 3 comprises an acceleration electrode 27 fading into a steel pipe 25 and penetrating a collimator configuration 31 schematically illustrated by a ring coil 33 and a yoke 35. Subsequent to passing the collimator configuration 31, the primary-electron beam traverses a pin hole 37 and a central hole 39 in a secondary-electron detector 41, whereupon the primary-electron beam 19 enters an objective lens 43 of the electron microscopy system 3. The objective lens 43 configured to focus the primary-electron beam 19 comprises a magnetic lens 45 and an electrostatic lens 47. In the schematic illustration of FIG. 2, the magnetic lens 45 comprises a ring coil 49, an inner pole shoe 51 and an outer pole shoe 53. The electrostatic lens 47 consists of a bottom end 55 of the steel pipe 29, the inner bottom end of the outer pole shoe 53 as well as a ring electrode 59 conically tapering towards position 11 at the object. The objective lens 43 schematically illustrated in FIG. 2 may comprise a composition as illustrated in more detail in U.S. Pat. No. 6,855,938.

Furthermore, the electron-microscopic system 3 may comprise a detector 41' for electrons having traversed the object in order to record an electron-microscopic image of the object from intensities of transmitted electrons, wherein the intensities are detected by the detector 41'.

The detector 41' for electrons having traversed the object is disposed on the side of the object region 11 opposite to the electron source 21. Accordingly, the distance between the detector 41' and the electron source 21 is larger than the distance between the object region 11 and the electron source 21.

The ion beam processing system 7 comprises an ion source 63 with an extraction electrode 65, a collimator 67, an adjustable aperture 69, deflection electrodes 71 and focusing lenses 73 configured to generate the ion beam 17 emerging from a housing 75 of the ion beam processing system 7.

The particle beam system 1 further comprises an object mount 81 configured to mount a TEM-sample to be manufactured in the object region 11 of the particle beam system 1. The object mount 81 comprises a shaft 83 protruding into the object region 11 and onto which the TEM-sample to be manufactured (not illustrated in FIG. 2) is mounted to. The shaft 83 is mounted to an inner part 85 of a pivot bearing 86 comprising an outer part 87 which is mounted to, for example, a vacuum casing of the particle beam system 1 and, hence, is fixedly disposed relative to the electron microscopy system 3 and the ion beam processing system 7. The inner part 85 of the pivot bearing is pivoted relative to the outer part 87 about an axis of rotation 89, wherein the shaft 83 of the object mount extends along the axis of rotation 89. In particular, the axis of rotation 89 may be oriented so that it intersects the object region 11 of the particle beam system 1. By rotating the shaft 83, the TEM-sample mounted to the shaft 83 of the object mount 81 may be rotated relative to the outer part 87 of the pivot bearing 86 about the axis of rotation 89 by more than 180°, as illustrated in FIG. 2 by arrow 91.

Furthermore, in order to position the TEM-sample in the object region 11, either the shaft 83 may be translationally moveable or tiltable relative to the outer part 87 or the outer part 87 may be translationally moveable or tiltable relative to the vacuum casing. Here, the shaft 83 may be coaxially moveable with respect to the axis of rotation 89 as well. In addition, the shaft 83 may also be moveable or tiltable in two directions being orthogonal to the axis of rotation 89.

Figure 3:
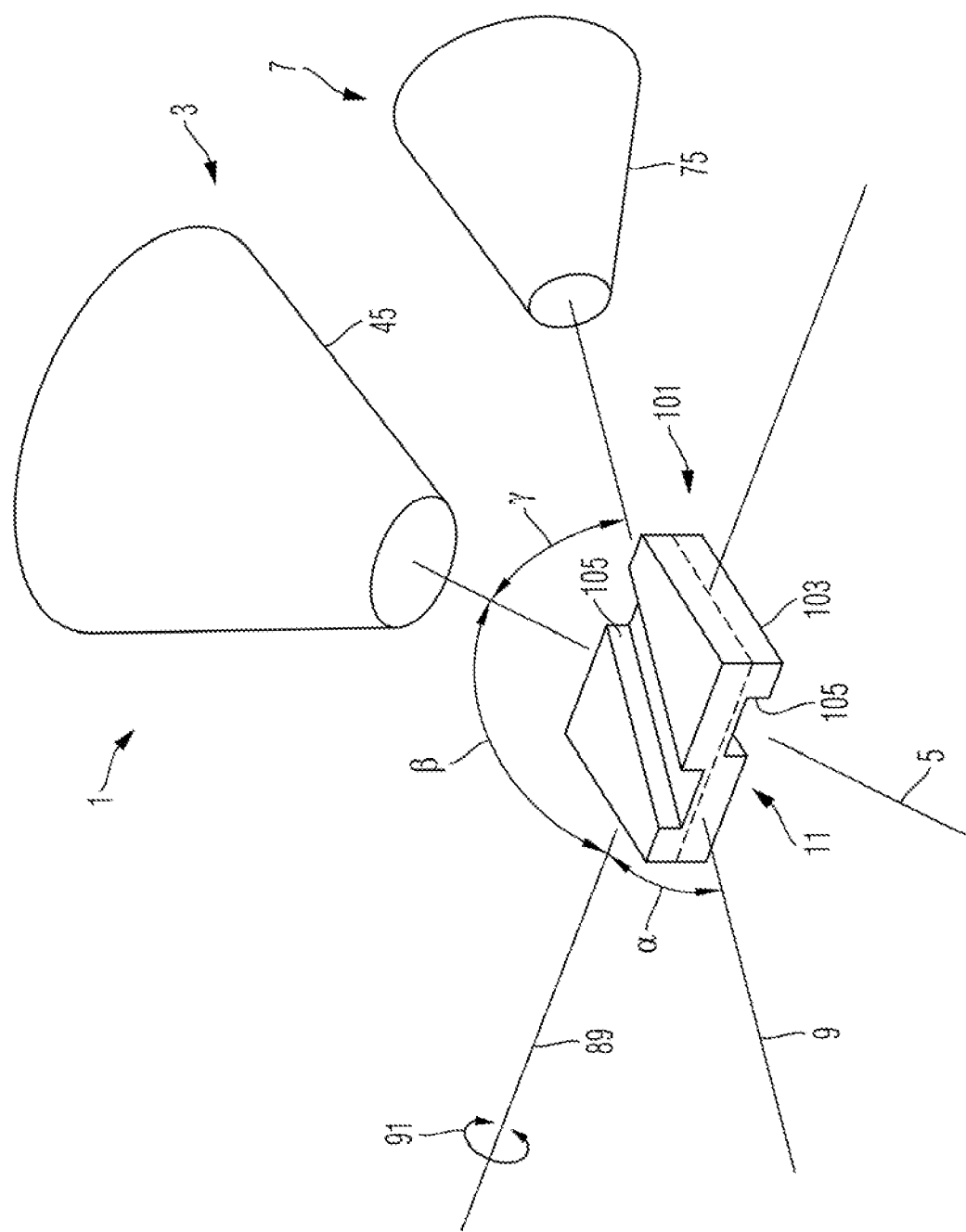
FIG. 3 is a schematic illustration for illustrating angle relations of the particle beam system of FIG. 2.

Geometric relations between the axis of rotation 89 of the object mount 81 and the main axis 5 of the electron microscopy system and the main axis 9 of the ion beam processing system are schematically illustrated in FIG. 3. Therein, of the electron microscopy system 3, merely a truncated conical, outer contour 45 of the objective lens and, of the ion beam processing system 7, merely a truncated conical outer contour 75 of the front casing are schematically illustrated in FIG. 3. However, a TEM-sample 101 is schematically illustrated in FIG. 3 which is disposed in the object region 11 of the particle beam system 1 and, there, is being mounted to the object mount 81 not illustrated in FIG. 3. The axis of rotation 89 of the object mount 81 and the main axis 9 of the ion beam processing system 7 being the direction from which the ion beam is incident onto the object region 11 enclose an angle α. In the illustrated embodiment, the angle α amounts to a value of 45°. The ion beam 9 can be directed to distinct locations within the object region 11 by controlling the deflectors 71 of the ion beam processing system 7 in order to form the strip-shaped recess 105 extending along the main axis 9 in the TEM-sample 101. The formation of the strip-shaped recess 105 may be monitored using the electron microscopy system 3 by capturing electron-microscopic images of the TEM-sample and the just formed recess 105. Here, the axis of rotation 89 of the object mount 81 is oriented at an angle β relative to the main axis 5 of the electron microscopy system 3 and, thus, relative to the direction from which the electrons are incident onto the object region 11, wherein the angle β amounts to a value of 90° in the illustrated embodiment.

As soon as the first of both the recesses 105 are formed, the object mount and, thus, the TEM-sample 101 mounted thereto are rotated by 180° about the axis of rotation 89 in order to form the second of both the recesses 105 using the ion beam.

In the illustrated embodiment, the angle α amounts to a value of 45°. As a consequence, the angle ε (see FIG. 1) between the strip-shaped recesses amounts to a value of 90°. However, deviations hereof will be possible, if the angle α amounts to different values which results in different values of the angle ε between the strip-shaped recesses, accordingly. For example, the angle α can amount to values between 35° and 55°. The angle β between the axis of rotation 89 and the direction of the electron beam amounts to a value of 90° in the illustrated embodiment in order to visualize a projection as large as possible of the surface of the TEM-sample 101 in electron-microscopic images. Though, other values of the angle β, for example, between 70° and 90°, can be chosen, too.

Figure 4:
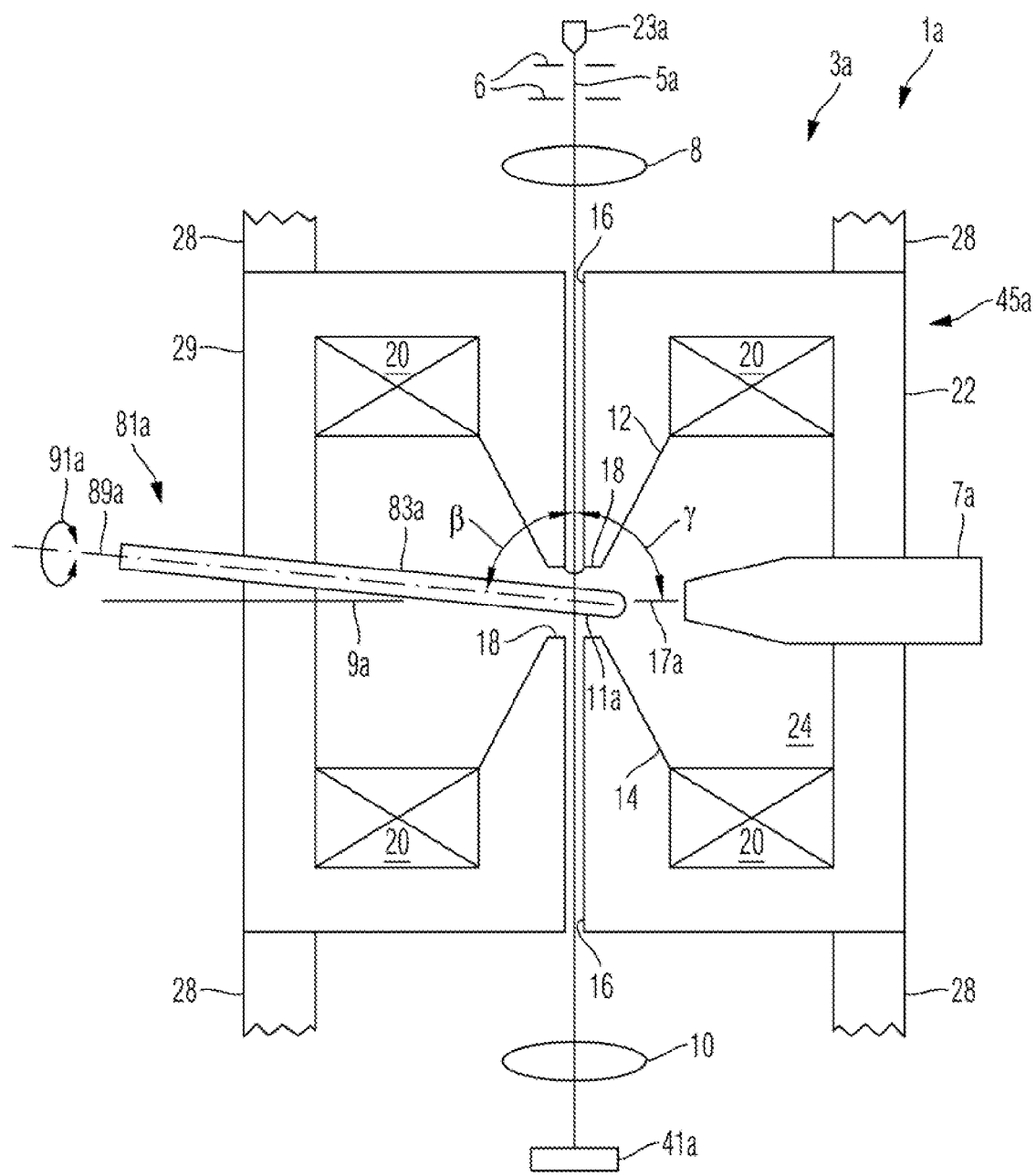
FIG. 4 is a schematic cross section of a particle beam system configured to analyze the TEM-sample illustrated in FIG. 1.

FIG. 4 illustrates another embodiment of a particle beam system configured to process and analyze a TEM-sample, respectively. The particle beam system 1a comprises a transmission electron microscope (TEM) 3a and an ion beam processing system 7a. The transmission electron microscope 3a serves for a transmission-electron-microscopic analysis of a TEM-sample (not illustrated in FIG. 4) mounted to an object mount 81a in an object region 11a. Here, the transmission electron microscope 3a comprises an electron-beam source 23a configured to generate an electron beam 5a, multiple electrodes 6 configured to form and to accelerate the beam 5a and one or multiple condenser lenses 8 or other electro-optical components for additional forming and manipulating of the beam 5a prior to its entry in an objective lens 45a. The other components may comprise a monochromator, a corrector for correcting optical errors of the lens 45a and deflectors for scanning the beam 9 across the object region 11a, for example.

In the bears path behind the lens 45a, further electro-optical components seen as projective lenses 10, apertures, phase plates, bi-prisms, correctors, spectrometers and the like and, at last, one or multiple detectors 41a can be disposed.

The lens 45a creates a magnetic field between two pole pieces 12, 14 focusing the electron beam 5a, wherein each of the pole pieces comprises a through-hole 16 traversed by the electron beam 5a. Each of the pole pieces 12, 14 tapers towards the object region 11a and comprises an end face 18 facing the object region 11a, wherein field lines of the focusing magnetic field emerge from and enter the end face, respectively. The magnetic field is created by a live coil 20 circumventing the pole pieces 12 and 14, respectively. The magnetic flux between the pole pieces 12, 14 is closed by a cylindrical, metallic yoke 22 also defining a vacuum space 24 including the object region 11a. In the illustration of FIG. 4, upwards towards the electron source 23a and downwards towards the detector 41a, further components 28 of the vacuum casing join the yoke 22 so that the electron source 23a and the detector 41a are also disposed within the vacuum.

The ion beam processing system a is mounted to the vacuum casing 22 so that an ion beam 17a generated by the ion beam processing system 7a is directed onto the object region 11a.

Figure 5:
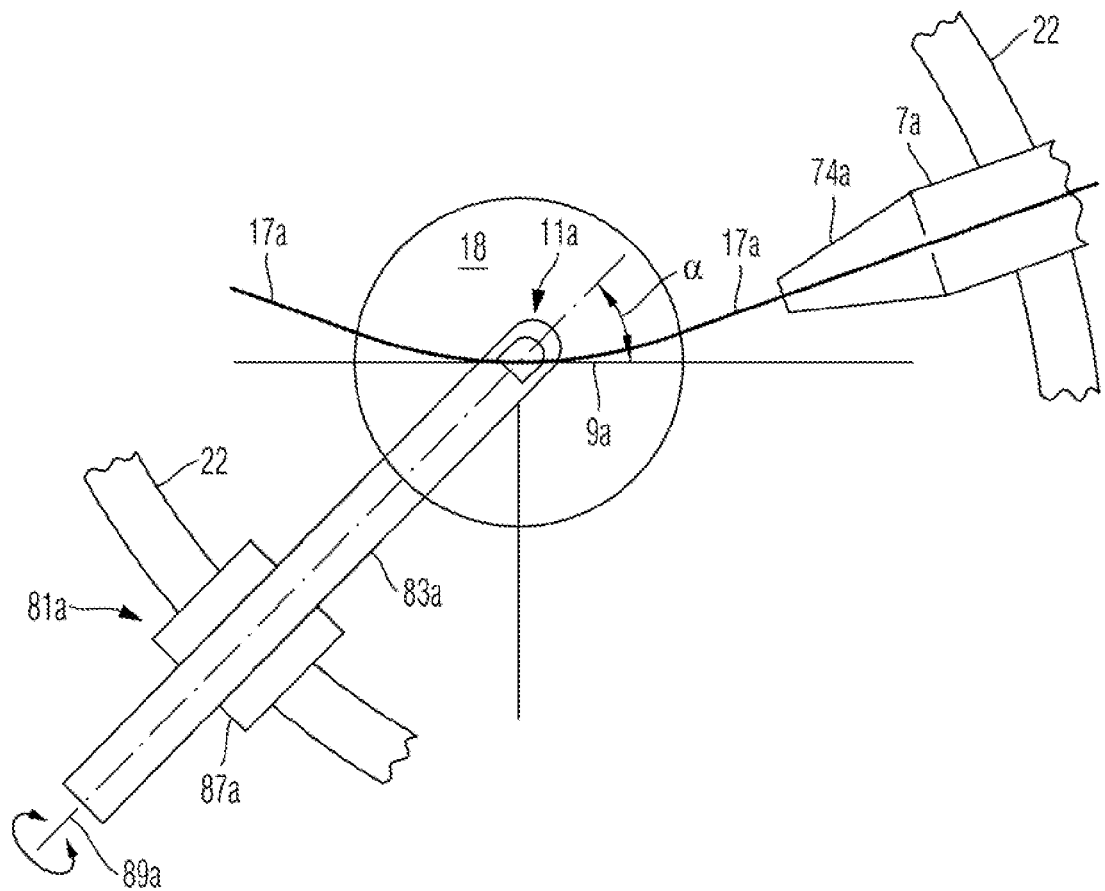
FIG. 5 is a schematic illustration for illustrating angle relations of the particle beam system illustrated in FIG. 4.

FIG. 5 illustrates a schematic top view onto a plane traversing the object region 11a and being orthogonally oriented to the direction of the electron beam 5a.

Due to the strong magnetic field between the end faces 18 of the pole pieces 12 and 14, the ions of the ion beam 17a move on a curved trajectory within the region of the magnetic field, wherein the trajectory substantially differs from a straight line. Hence, a direction 9a from which the ion beam 17a is incident onto the object region 11a is different from a direction from which the ion beam 17a emerges from the ion beam column of the ion beam processing system 7a.

The TEM-sample is mounted to a shaft 83a of an object mount 81a in the object region 11a. Here, the shaft 83a is rotatable about an axis of rotation 89a, wherein, an angle α between the axis of rotation 89a and the direction 9a from which the ion beam 17a is incident onto the object region 11a amounts to a value of 45° in the illustrated embodiment again. Nevertheless, thereof deviating values may also be chosen for the angle α.

An angle γ between the direction from which the electron beam 5a is incident onto the object region 11a and the direction 9a from which the ion beam 17a is incident onto the object region amounts to a value of 90° in the illustrated embodiment of the FIGS. 4 and 5. An angle β between the direction from which the electron beam 5a is incident onto the object region 11a and the axis of rotation 89a of the object mount 81a amounts to a value being slightly smaller than 90° so that the ion beam 17a is incident onto the thin region 107 (see FIG. 1) of the TEM-sample disposed in the object region 11a at a small angle so that a grazing incidence of the ion beam 17a occurs on the thin region 107. In the illustrated embodiment, the angle β amounts to a value of 87°.

According to an alternative embodiment, the angle β amounts to a value of 90° while the angle γ amounts to a value of less than 90° in order to achieve said grazing incidence onto the region 107 of the TEM-sample. Here, the angle γ may amount to a value of, for example, 87°.

The ion beam 17a may be, for example, an argon-ion beam serving to remove impurities from the TEM-sample mounted in the object region of the transmission electron microscope 3a. Here, the ion beam 17a is directed onto a side of the region 107 (see FIG. 1) of the TEM-sample until this side is substantially free of impurities. Then, the shaft 83a of the object mount together with the TEM-sample mounted thereto is rotated by 180° about the axis of rotation 89a whereupon the other side of the region 107 is exempted from impurities with the help of the ion beam 17a.

This process can be monitored by recording transmission-electron-microscopic images of the region 107 of the TEM-sample.

Figure 6:
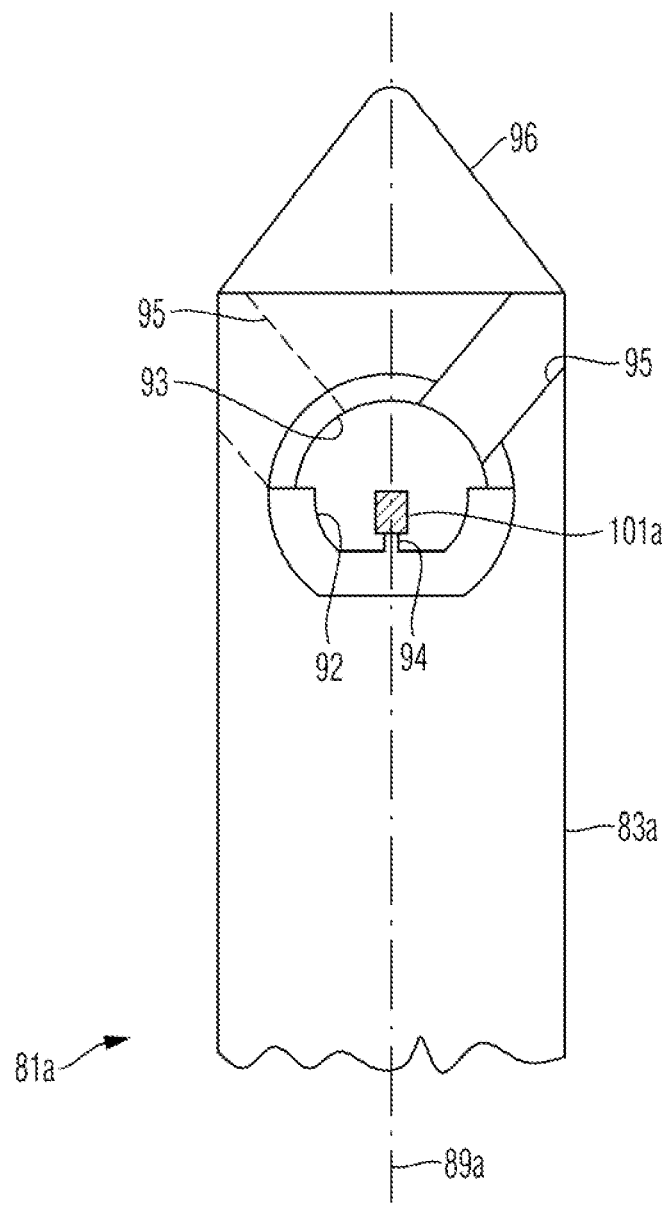
FIG. 6 is a schematic illustration of an object mount.

FIG. 6 illustrates a detailed view of a front part of the shaft 83a of the object mount 81a. The shaft 83a comprises a recess 93 into which an inset 93 is set, wherein the inset comprises a projection 94 which, if the inset 92 is set into the recess, will project into the recess 93 and to which the TEM-sample 101a is mounted to so that the TEM-sample is disposed within the recess 93 and can be traversed by the electron beam. Furthermore, the shaft 83a comprises a strip-shaped recess 95 configured to let the ion beam 17a be incident onto the TEM-sample 101a without shadowing the ion beam 17a by the material of the shaft 83a. A correspondent recess 95 is provided on the other side of the shaft 83a in order to let the ion beam 17a be incident onto the TEM-sample 101a after the shaft 83a has been rotated about the axis of rotation 89a by 180°. This strip-shaped recess 95 is illustrated by dashed lines in the top view of FIG. 6.

Furthermore, the shaft 83a may comprise a conical tip 96 borne by a counter bearing which can be intended to be disposed within the vacuum space 24 in order to provide a precise mount of the TEM-sample 101a.

For transferring the object from the cross-beam-system, into the transmission electron microscope, the entire object mount 81 together with the object can be removed from the cross-beam-system and be mounted in the transmission electron microscope so that the object is disposed in the transmission electron microscope. However, it is also possible that the object mount 81 in the cross-beam-system comprises an intake for the inset 92 to which the object is mounted to. In this case, merely the inset 92 together with the object can be removed from the cross-beam-system and transferred to the transmission electron microscope, where the inset 92 together with the object is mounted to the object mount 81a of the transmission electron microscope so that the object may be analysed using the transmission electron microscope.

Figure 7:
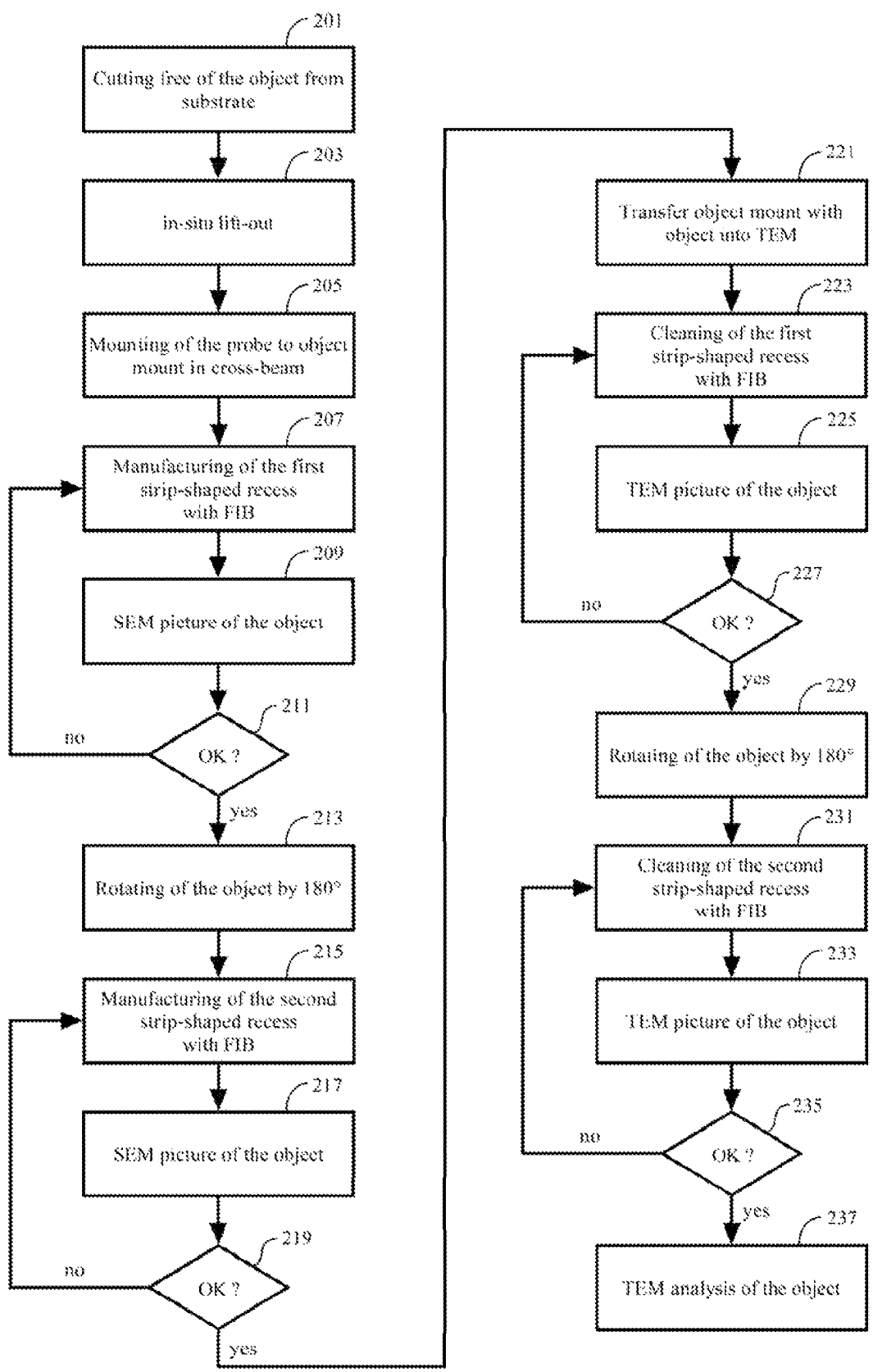
FIG. 7 is a flow chart of a method of processing and analyzing a TEM-sample.

In the following, a method of processing a TEM-sample and its analysis in a transmission electron microscope is illustrated referring to the flow chart of FIG. 7.

It is assumed that an interesting region exists in a larger substrate, wherein the interesting region shall be analysed with the help of a transmission electron microscope. In a step 201, a cuboid-shaped material object is cut free from the substrate, wherein the object comprises the interesting region. Here, the material object may exhibit a shape different from the cuboid shape, for example, a trapezoidal shape, a prism shape or a wedge shape.

In a step 203, the object is released from the substrate by means of a transfer tool. This process is also referred to by in-situ lift-out. Background information- regarding an in-situ lift-out method is given, for example, in EP 2 043 131 A2, wherein the full disclosure of this document is incorporated herein by reference. Then, in a step 205, with help of the transfer tool, the object is mounted to an object mount, for example, the object mount 83 illustrated in FIGS. 2 to 6, and the object mount is mounted in a particle beam system, for example, the cross-beam-system illustrated in FIG. 2. Thereupon, In a step 207, a first strip-shaped recess is formed in the object. The process of forming the recess may be monitored by recording an image of the object with help of the SSM in a step 209. In a step 211, it is decided whether the strip-shaped recess has been formed as desired, wherein the recess contains the interesting region. If this is not the case, a further processing using the ion beam is performed in the step 207. If the first strip-shaped recess has been formed as desired, the object is rotated by 180° in a step 213, wherein the axis in respect to which the rotation is performed and the direction from which the ion beam is incident onto the object region enclose an angle α. Here, the rotation may be performed by a single step of rotation about an axis of rotation. However, it is also possible to perform this rotation by multiple steps of movement which may comprise, for example, multiple consecutively executed rotations about distinct axes of rotation and translations in one or multiple directions.

After the rotation of the object, a second strip-shaped recess is formed with help of the ion beam in a step 215, wherein the second strip-shaped recess is disposed on the side of the object opposite to the side of the first strip-shaped recess and extends at an angle of, for example, 90° relative to the first strip-shaped recess. This process may again be monitored by recording an image of the object with help of the SEM in a step 217. In dependence of a decision step 219, the processing using the ion beam is continued in the step 215, if the desired shape of the second strip-shaped recess has not yet been achieved.

If the second strip-shaped recess has been formed as desired, the object comprises a thin region (region 107 in FIG. 1) which contains the interesting region and which may be analyzed with the help of at lease one of the SEM and the transmission electron microscope. For the analysis using the transmission electron microscope, then, in a step 221, the object is transferred into the transmission electron microscope, for example, the particle beam system illustrated in the FIGS. 4 and 5. Here, the object may be disposed in an evacuated transfer container. Notwithstanding, it is possible that the object is contaminated by this transfer, for example, by oxidation. Hence, in a step 223, the first strip-shaped recess and, thus, the one surface of the thin region 107 of the object is cleaned with help of the ion beam 17a. Again this process may be monitored by recording a transmission-electron-microscopic image of the object in a step 225. In dependence of the recorded image, it is decided in a step 227, whether the processing using the ion beam in the step 223 shall be continued or whether the other side of the region 107 shall be cleaned. Here, in a step 229, the object is rotated about an axis by 180° wherein the axis and the direction from which the ion beam is incident onto the object enclose an angle α of, for example, 45°.

Thereafter, in a step 231, the second strip-shaped recess and, thus, the second side of the thin region 107 is cleaned. Again this process may be monitored by recording an image of the region 107 with help of the transmission electron microscope in a step 233. In dependence thereof, it is decided in a decision step 235, whether the processing using the ion beam shall be continued in the step 231 or whether the object is in a state in which the transmission-electron-microscopic analysis of the interesting region of the object can begin. If this is the case, the transmission-electron-microscopic analysis of the object is performed in a step 237.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

What is claimed is:

1. A particle beam system, comprising:
 a first particle beam column configured to generate a first particle beam incident onto an object region from a first direction, wherein the first particle beam is an ion beam;
 a second particle beam column configured to generate a second particle beam incident onto the object region from a second direction; and
 an object mount configured to mount an object in the object region, wherein the object mount comprises a shaft rotatable with respect to the first particle beam column about an axis of rotation;
 wherein the following relation is fulfilled:

$$35° \leq \alpha \leq 55°,$$

wherein α denotes a first angle between the first direction and the axis of rotation.

2. The particle beam system according to claim 1, wherein the following relation is fulfilled:

$$70° \leq \beta \leq 90°,$$

wherein β denotes a second angle between the axis of rotation and the second direction.

3. The particle beam system according to claim 1, wherein the axis of rotation intersects the object region.

4. The particle beam system according to claim 1, wherein the following relation is fulfilled:

$$20° \leq \gamma \leq 90°,$$

wherein γ denotes a third angle between the first direction and the second direction.

5. The particle beam system according to claim 1, wherein the second particle beam column comprises a beam deflector configured to scan the second particle beam across the object region and a detector configured to detect particles emanating from the object region.

6. The particle beam system according to claim 1, wherein the second particle beam is an electron beam.

7. The particle beam system according to claim 6, wherein the second particle beam column comprises a SEM.

8. The particle beam system according to claim 6, wherein the second particle beam column comprises a TEM.

9. The particle beam system according to claim 8, wherein one of the following relations is fulfilled:

$$(\beta=90° \text{ and } \gamma \leq 88°),$$

wherein β denotes the second angle between the axis of rotation and the second direction and γ denotes the third angle between the first direction and the second direction.

10. A method of processing a TEM-sample, wherein the method comprises:
   mounting an object in a first particle beam system such that the object is disposed in an object region of the first particle beam system;
   a first directing of a first particle beam onto the object region from a first direction, wherein the first particle beam is an ion beam; and then
   rotating the object about an axis by 180°, wherein the following relation is fulfilled:

$$35° \leq \alpha \leq 55°,$$

wherein α denotes a first angle between the first direction and the axis of rotation; and then
   a second directing of the first particle beam onto the object region from the first direction;
wherein material is removed from the object during the first directing and the second directing of the first particle beam onto the object region.

11. The method according to claim 10, further comprising a third directing of a second particle beam onto the object region and detecting particles emanating from the object region.

12. The method according to claim 11, wherein at least one of the first directing and the second directing of the first particle beam onto the object region is performed based on the particles detected during the third directing of the second particle beam onto the object region.

13. The method according to claim 10, wherein the first particle beam is a gallium-ion beam.

14. The method according to claim 10, wherein a strip-shaped recess is formed in the object during each of the first directing and the second directing of the first particle beam onto the object region.

15. The method according to claim 14, wherein the second particle beam is an electron beam generated by a SEM, and wherein the method further comprises:
   mounting the object in a second particle beam system such that the object is disposed in an object region of the second particle beam system;
   a fourth directing of a third particle beam onto the object region from a fourth direction, wherein the third particle beam is an ion beam; and then
   rotating the object about an axis by 180°, wherein the following relation is fulfilled:

$$35° \leq \alpha \leq 55°,$$

wherein α denotes the first angle between the first direction and the axis of rotation; and then
   a fifth directing of the third particle beam onto the object region from the fourth direction; and then
   a sixth directing of a fourth particle beam onto the object region and detecting the particles transmitted through the object;
wherein material is removed from the object during the fourth directing and the fifth directing of the third particle beam onto the object region and
wherein the fourth particle beam is an electron beam generated by a TEM.

16. The method according to claim 15, wherein the third particle beam is an argon-ion beam.

17. The particle beam system according to claim 1, wherein the following relation is fulfilled:

$$30° \leq \gamma \leq 60°,$$

wherein γ denotes a third angle between the first direction and the second direction.

18. The particle beam system according to claim 8, wherein one of the following relations is fulfilled:

$$(\beta \leq 88° \text{ and } \gamma=90°),$$

wherein β denotes the second angle between the axis of rotation and the second direction and γ denotes the third angle between the first direction and the second direction.

\* \* \* \* \*

UNITED STATES PATENT AND TRADEMARK OFFICE
CERTIFICATE OF CORRECTION

| | |
|---|---|
| PATENT NO. | : 8,835,843 B2 |
| APPLICATION NO. | : 14/057002 |
| DATED | : September 16, 2014 |
| INVENTOR(S) | : Lorenz Lechner |

It is certified that error appears in the above-identified patent and that said Letters Patent is hereby corrected as shown below:

In the Specification

| | | |
|---|---|---|
| Column 1, | line 30, | "0185813" should read --0189813--; |
| | line 52, | "forcing" should read --forming--; |
| | line 63, | "0185813" should read --0189813--. |
| Column 2, | line 23, | "used," should read --used--. |
| Column 4, | line 28, | "Of" should read --of--; |
| | line 37, | "bears" should read --beam--; |
| | line 44, | "beam," should read --beam--. |
| Column 5, | line 34, | "25" should read --29--. |
| Column 6, | line 33, | "conical," should read --conical--. |
| Column 7, | line 28, | "bears" should read --beam--; |
| | line 29, | "seen" should read --such--; |
| | line 48, | "a" should read --7a--. |
| Column 8, | line 38, | "inset 93" should read --inset 92--; |
| | line 56, | "cross-beam-system," should read --cross-beam-system--. |
| Column 9, | line 16, | "information-" should read --information--; |
| | line 24, | ", In" should read --, in--; |
| | line 26, | "SSM" should read --SEM--; |
| | line 55, | "lease" should read --least--. |

Signed and Sealed this
Third Day of March, 2015

Michelle K. Lee
*Deputy Director of the United States Patent and Trademark Office*